United States Patent
Moghari et al.

(10) Patent No.: US 11,790,597 B2
(45) Date of Patent: Oct. 17, 2023

(54) METHODS FOR THREE-DIMENSIONAL CARDIAC IMAGING

(71) Applicant: THE CHILDREN'S MEDICAL CENTER CORPORATION, Boston, MA (US)

(72) Inventors: Mehdi H. Moghari, Boston, MA (US); Andrew J. Powell, Boston, MA (US); Tal Geva, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 463 days.

(21) Appl. No.: 16/647,784

(22) PCT Filed: Sep. 25, 2018

(86) PCT No.: PCT/US2018/052667
§ 371 (c)(1),
(2) Date: Mar. 16, 2020

(87) PCT Pub. No.: WO2019/067449
PCT Pub. Date: Apr. 4, 2019

(65) Prior Publication Data
US 2020/0234485 A1    Jul. 23, 2020

Related U.S. Application Data

(60) Provisional application No. 62/563,479, filed on Sep. 26, 2017.

(51) Int. Cl.
*G06K 9/00* (2022.01)
*G06T 15/08* (2011.01)
*A61B 5/00* (2006.01)
*A61B 5/055* (2006.01)
*A61B 5/113* (2006.01)

(52) U.S. Cl.
CPC ............ *G06T 15/08* (2013.01); *A61B 5/0044* (2013.01); *A61B 5/055* (2013.01); *A61B 5/113* (2013.01); *A61B 5/7289* (2013.01); *G06T 2210/41* (2013.01)

(58) Field of Classification Search
CPC . G06T 2207/10072; G06T 2207/10076; G06T 2207/10081; G01N 23/046; G01R 33/20; G01R 33/5608
See application file for complete search history.

(56) References Cited

U.S. PATENT DOCUMENTS

2009/0148021 A1    6/2009  Yui
2010/0222666 A1*   9/2010  Foo ........................ A61B 5/055
                                                        600/413

OTHER PUBLICATIONS

Moghari, Mehdi H., Tal Geva, and Andrew J. Powell. "Prospective heart tracking for whole-heart magnetic resonance angiography." Magnetic resonance in medicine 77.2 (2017): 759-765. (Year: 2016).*

(Continued)

*Primary Examiner* — Avinash Yentrapati
(74) *Attorney, Agent, or Firm* — Melissa Hunter-Ensor; Kristopher Reichlen; Greenberg Traurig, LLP

(57) ABSTRACT

The invention features a prospective respiratory motion compensation technique for cardiovascular magnetic resonance imaging of the whole-heart of a free-breathing subject.

20 Claims, 7 Drawing Sheets

(56) References Cited

OTHER PUBLICATIONS

International Search Report and Written Opinion in PCT Patent Application No. PCT/US2018/052667, dated Jan. 16, 2019 (10 pages).
Arai et al., "Visualization of Aortic Valve Leaflets Using Black Blood MRI," Journal of Magnetic Resonance Imaging, 1999, vol. 10, pp. 771-777.
Blalock et al., "Interstudy Variability in Cardiac Magnetic Resonance Imaging Measurements of Ventricular Volume, Mass, and Ejection Fraction in Repaired Tetralogy of Fallot: A Prospective Observational Study," Journal of Magnetic Resonance Imaging, 2013, vol. 38, pp. 829-835.
Bland et al., "Statistical Methods For Assessing Agreement Between Two Methods Of Clinical Measurement," Lancet, 1986, vol. i, pp. 307-310.
Hamdan et al., "Single-Breathhold Four-Dimensional Assessment of Left Ventricular Volumes and Function Using k-t BLAST After Application of Extracellular Contrast Agent at 3 Tesla," Journal of Magnetic Resonance Imaging, 2008, vol. 27, pp. 1028-1036.
Hamlet et al., "An interactive videogame designed to improve respiratory navigator efficiency in children undergoing cardiovascular magnetic resonance," Journal of Cardiovascular Magnetic Resonance, 2016, vol. 18, Article No. 54, pp. 1-10.
Makowski et al., "Single breath-hold assessment of cardiac function using an accelerated 3D single breath-hold acquisition technique—comparison of an intravascular and extravascular contrast agent," Journal of Cardiovascular Magnetic Resonance, 2012, vol. 14, Article No. 53, pp. 1-8.
Matthew et al., "Quantitative analysis of cardiac left ventricular variables obtained by MRI at 3 T: a pre- and post-contrast comparison," The British Journal of Radiology, Jul. 2012, vol. 85, pp. e343-e347.
Miller et al., "MR Imaging of the Heart with Cine True Fast Imaging with Steady-State Precession: Influence of Spatial and Temporal Resolutions on Left Ventricular Functional Parameters," Radiology, 2002, vol. 223, pp. 263-269.
Nezafat et al., "Inflow Quantification in Three-Dimensional Cardiovascular MR Imaging," Journal of Magnetic Resonance Imaging, 2008, vol. 28, pp. 1273-1279.
Piccini et al., "Respiratory Self-Navigation for Whole-Heart Bright-Blood Coronary MRI: Methods for Robust Isolation and Automatic Segmentation of the Blood Pool," Magnetic Resonance in Medicine, 2012, vol. 68, pp. 571-579.
Pruessmann et al., "SENSE: Sensitivity Encoding for Fast MRI," Magnetic Resonance in Medicine, 1999, vol. 42, pp. 952-962.
Uecker et al., "ESPIRiT—An Eigenvalue Approach to Autocalibrating Parallel MRI: Where SENSE Meets GRAPPA," Magnetic Resonance in Medicine, 2014, vol. 71, pp. 990-1001.
Fok et al., "Accelerated free-breathing 3D whole-heart magnetic resonance angiography with a radial phyllotaxis trajectory, compressed sensing, and curvelet transform," Magnetic Resonance Imaging, 2021, vol. 83, pp. 57-67.
Moghari et al., "Accelerated Whole-Heart MR Angiography Using a Variable-Density Poisson-Disc Undersampling Pattern and Compressed Sensing Reconstruction," Magnetic Resonance in Medicine, 2018, vol. 79, pp. 761-769.
Moghari et al., "Cardiac magnetic resonance using fused 3D cine and 4D flow sequences: Validation of ventricular and blood flow measurements," Magnetic Resonance Imaging, 2020, vol. 74, pp. 203-212.
Moghari et al., "Free-Breathing Whole-Heart 3D Cine Magnetic Resonance Imaging With Prospective Respiratory Motion Compensation," Magnetic Resonance in Medicine, 2018, vol. 80, pp. 181-189.

\* cited by examiner

METHODS FOR THREE-DIMENSIONAL CARDIAC IMAGING

This application is the U.S. national phase application, pursuant to 35 U.S.C. § 371, of PCT international application Ser. No.: PCT/US2018/052667, filed Sep. 25, 2018, designating the United States and published in English, which claims the benefit of the following U.S. Provisional Application No. 62/563,479, filed Sep. 26, 2017, the entire contents of which are incorporated herein by reference.

STATEMENT OF RIGHTS TO INVENTIONS MADE UNDER FEDERALLY SPONSORED RESEARCH

This invention was made with government support under Grant No. KL2 TR001100 awarded by the National Institutes of Health. The government has certain rights in the invention.

BACKGROUND OF THE INVENTION

A two-dimension (2D) cine steady-state free precession (SSFP) sequence is the established method in cardiovascular magnetic resonance imaging (MRI) for the assessment of heart motion and quantitation of ventricular volumes and ejection fraction. Conventionally, 2-4 ventricular long-axis slices and a stack of 10-15 ventricular short-axis slices are precisely planned to encompass both ventricles. One or two slices at a time are acquired while the patient holds their breath for 5-15 seconds to minimize respiratory motion artifact. This approach, however, has several widely-recognized drawbacks. The technique requires careful planning of multiple imaging planes by a knowledgeable operator, and repeated breath-hold instructions. In addition, the through-plane resolution is inferior to the in-plane resolution and, thus, stacks of contiguous slices are poorly suited for reformatting in other planes. As a result, one must image the ventricles in multiple orientations, and with this comes a requirement for careful slice location planning by expert operators. Moreover, breath-holding may not be feasible in ill or younger patients. Even patients who can hold their breath may have difficulty achieving a consistent amplitude of breath-holding leading to slice-to-slice misregistration and errors in ventricular volume measurements.

An isotropic non-angulated three-dimensional (3D) cine SSFP sequence addresses some of the drawbacks of 2D slices as it is easy to plan, and once acquired, can be reformatted in multiple appropriate planes for interpretation and quantification. Acceleration techniques, such as parallel imaging, and compressed sensing, have been used to acquire 3D cine SSFP dataset in a single breath-hold. However, shortening the acquisition time to a breath-hold also requires sacrificing spatial and temporal resolution beyond that which is optimal for accurate measurements of left and right ventricular parameters and, therefore, this approach has not become the clinical routine. Thus, a need exists for new methods related to cardiovascular Mill and the assessment of heart motion.

SUMMARY OF THE INVENTION

As described herein, the present invention features a prospective respiratory motion compensation method for imaging (e.g., cardiovascular magnetic resonance imaging, ultrasound, or computerized tomography (CT)) of the whole-heart of a free-breathing subject. In one embodiment, the method involves tracking the respiratory-induced motion by three-dimensional cine steady-state free precession (SSFP) imaging during the four excitations (Heart-NAVs) of a cardiac cycle.

In one aspect, the present invention provides a method for obtaining a three-dimensional reconstruction of a heart in a freely respiring subject, the method involving acquiring three-dimensional images of the heart during respiration of a subject; plotting in one-dimension respiratory induced displacement of the heart in the superior-inferior orientation during respiration, wherein the maximal superior displacement of the heart defines a respiratory acceptance window having a specified width; and selecting a series of three-dimensional images of the heart that fall within the acceptance window for use in reconstruction, thereby obtaining a three-dimensional reconstruction of the heart.

In another aspect, the present invention provides a method for obtaining a three-dimensional reconstruction of a heart in a freely respiring subject, the method involving tracking the respiratory-induced motion of the heart in the superior-inferior orientation during the course of respiration of a subject using 3D cine steady-state free precession (SSFP) imaging, wherein a respiratory-induced motions is acquired during a four radio-frequency image excitation.

One aspect provides a method for obtaining a three-dimensional reconstruction of a heart in a freely respiring subject, the method comprising acquiring three-dimensional images of the heart with and without phase contrast during respiration of a subject; plotting in one-dimension respiratory induced displacement of the heart in the superior-inferior orientation during respiration, wherein the maximal superior displacement of the heart defines a respiratory acceptance window having a specified width; selecting a series of three-dimensional images of the heart that fall within the acceptance window for use in reconstruction; and fusing the acquired images, thereby obtaining a three-dimensional reconstruction of the heart.

In various embodiments of any aspect delineated herein, the images are acquired using cardiovascular magnetic resonance imaging, ultrasound, or computerized tomography (CT) scan. In various embodiments, the image acquisition is carried out using three-dimensional (3D) cine steady-state free precession sequence imaging. In some embodiments, a radiofrequency pulse is modified so that the phase-encoding gradient is turned off and a center-line of k-space along the superior-inferior direction is read. In some embodiments, the method is carried out at the beginning of every $5^{th}$ phase segment of the cardiac cycle. In various embodiments of any aspect delineated herein, the plot comprises a one-dimensional projection line of the 3D SSFP imaging volume in the superior-inferior orientation.

In various embodiments of any aspect delineated herein, the image data is processed and displayed. In various embodiments, the width of the respiratory acceptance window is at least 5 mm. In various embodiments, the width of the respiratory acceptance window is at least 7 mm. In various embodiments, the width of the respiratory acceptance window is at least 10 mm.

In various embodiments of any aspect delineated herein, the mean scan time is between about 4 and 7 minutes. In various embodiments, the scan time of 3D cine acquisition is shortened by parallel imaging with sensitivity encoding (SENSE). In various embodiments, the 3D cine SSFP is acquired in a sagittal orientation.

In various embodiments of any aspect delineated herein, the scan time is less than 10 minutes. In some embodiments, the images have a lower ventricular blood-to-myocardium contrast ratio and contrast-to-noise ratio than conventionally acquired images. In some embodiments, the method is compatible with retrospective cardiac gating.

In various embodiments of any aspect delineated herein, the method is carried out after administration of a contrast agent to the subject. In some embodiments, the contrast agent is gadolinium-based. In some embodiments, the gadolinium-based contrast agent is selected from the group consisting of gadoterate, gadodiamide, gadobenate, gadopentetate, gadoteridol, gadoversetamide, gadoxetate, gadobutrol, and gadofosveset.

In various embodiments of any aspect delineated herein, the subject is a child, is anesthetized, or is otherwise incapable of holding their breath.

In various embodiments of any aspect delineated herein, the method characterizes a cardiovascular disorder selected from the group consisting of tissue damage associated with a heart attack, reduced blood flow in the heart muscle, cardiac function and ejection fraction, aortic tears, aneurysms, narrowing, cardiomyopathy, diseases of the pericardium, heart disease, heart valve disorders, congenital heart problems, connective tissue disorders.

In various embodiments of any aspect delineated herein, the method characterizes a surgical repair of the heart.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "cine steady state free precession (SSFP)" is meant a gradient echo MRI pulse sequence in which a steady, residual transverse magnetization is maintained between successive cycles.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ. Examples of diseases include tissue damage associated with a heart attack, reduced blood flow in the heart muscle, cardiac function and ejection fraction, aortic tears, aneurysms, or narrowing, cardiomyopathy, diseases of the pericardium (e.g., constrictive pericarditis), heart disease (e.g., heart failure, enlargement of the heart, abnormal growths including cancerous tumors), heart valve disorders (e.g., regurgitation, aortic valve stenosis and/or regurgitation, atrial septal defect, Ebstein anomaly of the tricuspid valve), congenital heart problems, as well as connective tissue disorders. In certain embodiments, a method of the invention is used to assess a surgical repair of the heart, e.g., repaired tetralogy of Fallot, repaired transposition of the great arteries, or, repaired double-outlet right ventricle.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention features a prospective respiratory motion compensation technique for imaging (e.g., cardiovascular magnetic resonance imaging, ultrasound, or computerized tomography (CT) scan) of the whole-heart of a free-breathing subject.

Figure 6:
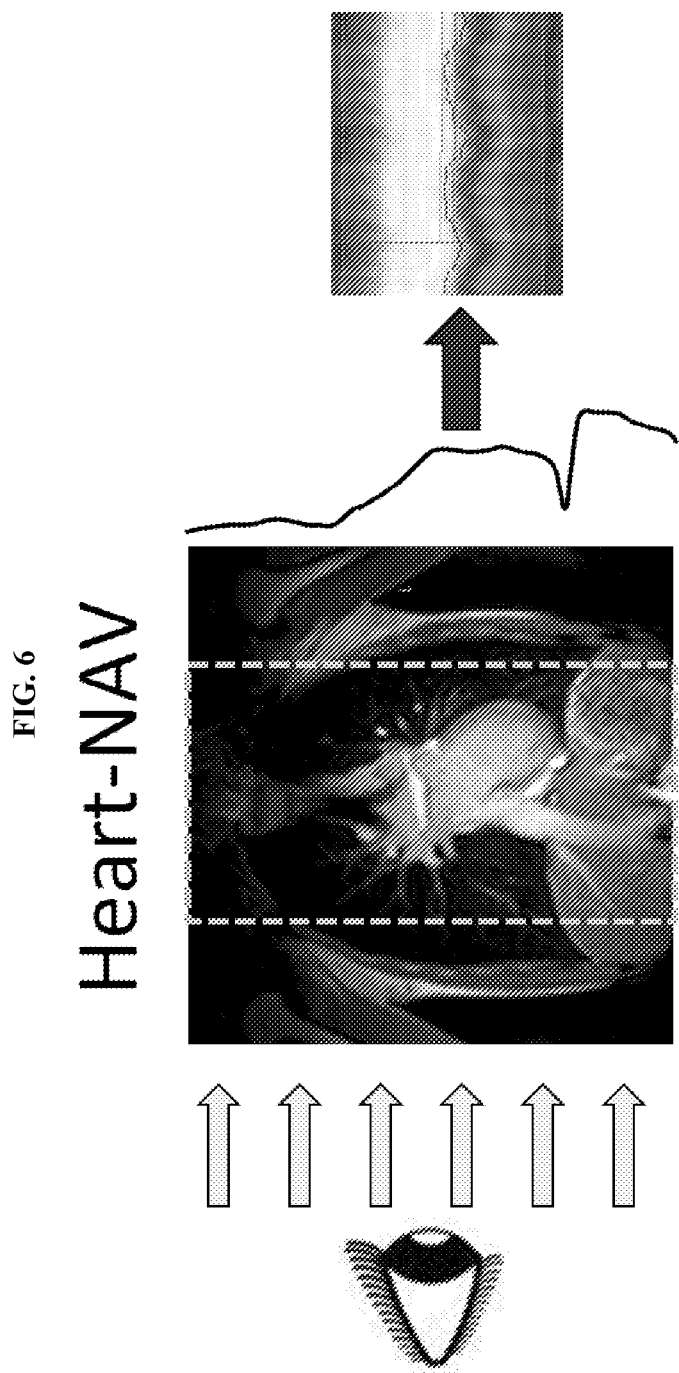
FIG. 6 provides an image that shows the vertical motion of the heart.

As reported in detail below, a series of experiments was carried out to develop and validate a new prospective respiratory motion compensation algorithm for free-breathing whole-heart three-dimensional cine steady-state free precession (SSFP) imaging. In a three-dimensional cine SSFP sequence, four radio-frequency excitation pulses per cardiac cycle which are commonly used for acquiring cine images, are re-purposed to prospectively track heart position (FIG. 6). Specifically, their 1D image is reconstructed and routed into the scanner's standard diaphragmatic navigator processing system. If all four signals are in end-expiration, cine image data from the entire cardiac cycle is accepted for image reconstruction. Prospective validation was performed in patients (n=17) by comparing in each a conventional breath-hold two-dimensional cine ventricular short-axis stack and a free-breathing whole-heart three-dimensional cine dataset.

All 3D cine SSFP acquisitions were successful and the mean scan time was 5.9±2.7 minutes. Left and right ventricular end-diastolic, end-systolic, and stroke volumes by 3D cine SSFP were all larger than those from 2D cine SSFP. This bias was <6% except for right ventricular end-systolic volume which was 12%. The 3D cine images had a lower ventricular blood-to-myocardium contrast ratio and contrast-to-noise ratio. Advantageously, the novel prospective respiratory motion compensation method for 3D cine SSFP imaging was robust and efficient, and yielded slightly larger ventricular volumes compared to breath-hold 2D cine imaging.

Cardiovascular Imaging

Cardiovascular magnetic resonance imaging, ultrasound, or computerized tomography (CT) scans are useful for visualizing and analyzing the heart. For example, cardiovascular magnetic resonance imaging (MRI) of the heart is a noninvasive and painless cardiovascular medical technique for detailed visualization and analysis that uses a magnetic field and radio waves to produce detailed images of the heart. The MRI scan does not use radiation. In some cases, a dye (contrast dye) or contrast material (e.g., iodine, barium, or gadolinium) is used during the MRI to allow visualization of the heart structures (e.g., blood vessels and tissue) more clearly. The MRI is possible because the human body is largely composed of water molecules, each containing two hydrogen nuclei, or protons. When inside the magnetic field (Bo) of the scanner, the magnetic moments of these protons align with the direction of the field. A radio frequency pulse is applied causing the protons to alter their magnetization alignment relative to the magnetic field. In response to the force bringing them back to their equilibrium orientation, the protons undergo a rotating motion (precession. These changes in magnetization alignment cause a changing magnetic flux, which yields a changing voltage in receiver coils to give a signal. The frequency at which a proton or group of protons in a voxel resonates depends on the strength of the local magnetic field around the proton or group of protons. By applying additional magnetic fields (gradients) that vary linearly over space, specific slices to be imaged can be selected, and an image is obtained by taking the 2-D Fourier transform of the spatial frequencies of the signal. This is also known as the "k-space," which is the 2D or 3D Fourier transform of the measured MR image.

During a cardiovascular MIII scan, a computer is used to generate clear, cross-sectional black and white images of the heart. These images can be converted into three-dimensional (3-D) pictures of the scanned area. Over the past several years, there has been a marked increase in the use of cardiovascular magnetic resonance for the anatomical and functional evaluation of heart disease. Cardiovascular magnetic resonance often complements echocardiography, provides a non-invasive alternative to x-ray angiography, avoids the ionizing radiation exposure of computed tomography, and overcomes many of the limitations of these modalities. Breath-hold, multi-slice 2D-cine cardiac MRI has been the standard approach for assessment of ventricular function in the clinic. This technique however has several drawbacks, including the requirement of careful planning of multiple imaging planes by a knowledgeable operator, and repeated breath-hold instructions to the patient. In addition, young and ill patients may not be able to breath-hold leading to a poor imaging quality. To address these deficiencies, a novel prospective respiratory motion compensation technique was developed for high spatiotemporal resolution 3D-cine whole-heart imaging during free-breathing.

The invention provides methods that are useful for imaging (cardiovascular magnetic resonance imaging, ultrasound, or computerized tomography (CT) scan) of the whole-heart of a free-breathing subject. In one embodiment, the methods generally involve tracking the respiratory-induced motion by 3D cine steady-state free precession (SSFP) imaging during the four excitations (Heart-NAVs) of a cardiac cycle. Parallel imaging with sensitivity encoding (SENSE) (Pruessmann K. P. et al., Magn Reson Med 1999; 42(5):952-962) is used to shorten the acquisition time so that it is suitable for the clinical environment. 3D cine and conventional 2D cine SSFP acquisitions are compared with regard to blood-to-myocardium contrast ratio, contrast-to-noise ratio, and ventricular volumes.

The methods of the invention may include the use of a contrast agent. For example, an intravascular (i.e., blood pool) or extracellular contrast agent. In one embodiment, the extracellular contrast agent is gadolinium based. In one embodiment, the intravascular agent is a gadolinium-chelate linked to albumin, dextran, or polylysine, is P792, gadomer-17, MS-325, MP-2269, B-22956, Gd-BOPTA, or an NACA.

Methods of the invention are useful for diagnosing or characterizing a variety of heart conditions. In particular, methods described herein are used for the diagnosis or characterization of tissue damage associated with a heart attack, reduced blood flow in the heart muscle, cardiac function and ejection fraction, aortic tears, aneurysms, or narrowing, diseases of the pericardium (e.g., constrictive pericarditis), heart disease (e.g., heart failure, enlargement of the heart, abnormal growths including cancerous tumors), heart valve disorders (e.g., regurgitation), and congenital heart problems.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Whole-Heart 3D Cine SSFP Sequence with Heart-NAV

Figure 1:
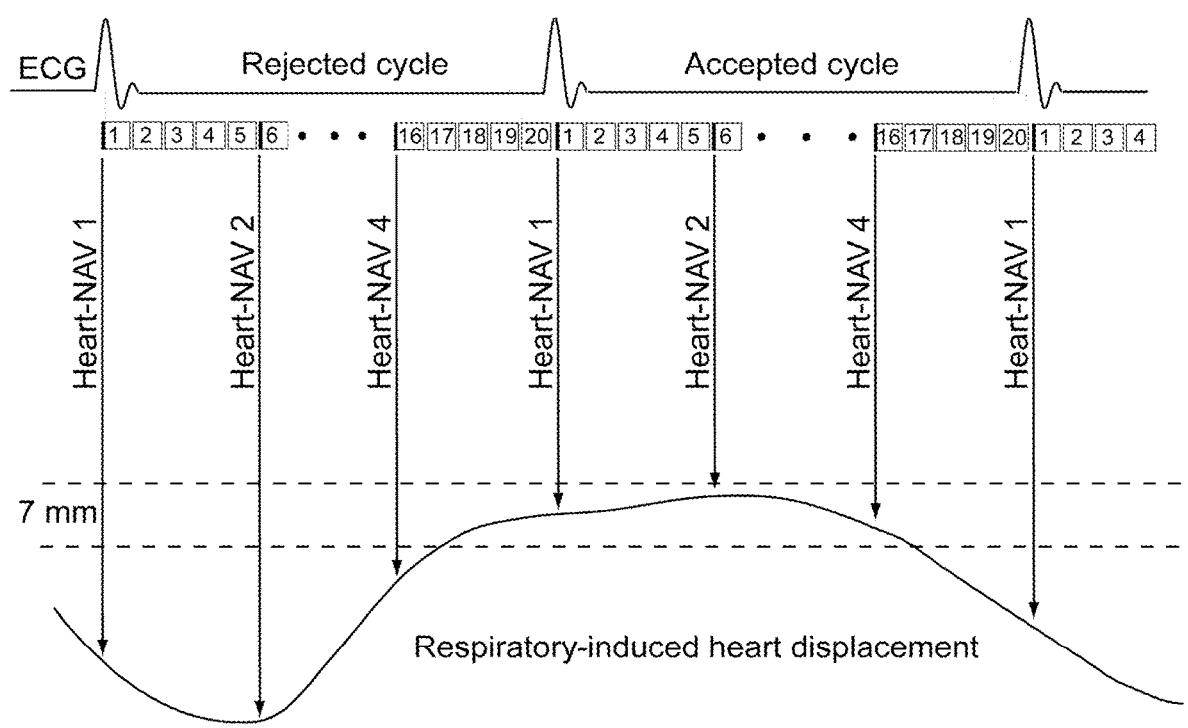
FIG. 1 depicts a diagram of the technique described herein (termed Heart-NAV) to prospectively gate and track the respiratory motion of the heart during a whole-heart three-dimensional cine steady-state free precession (SSFP) sequence.
Figure 2:
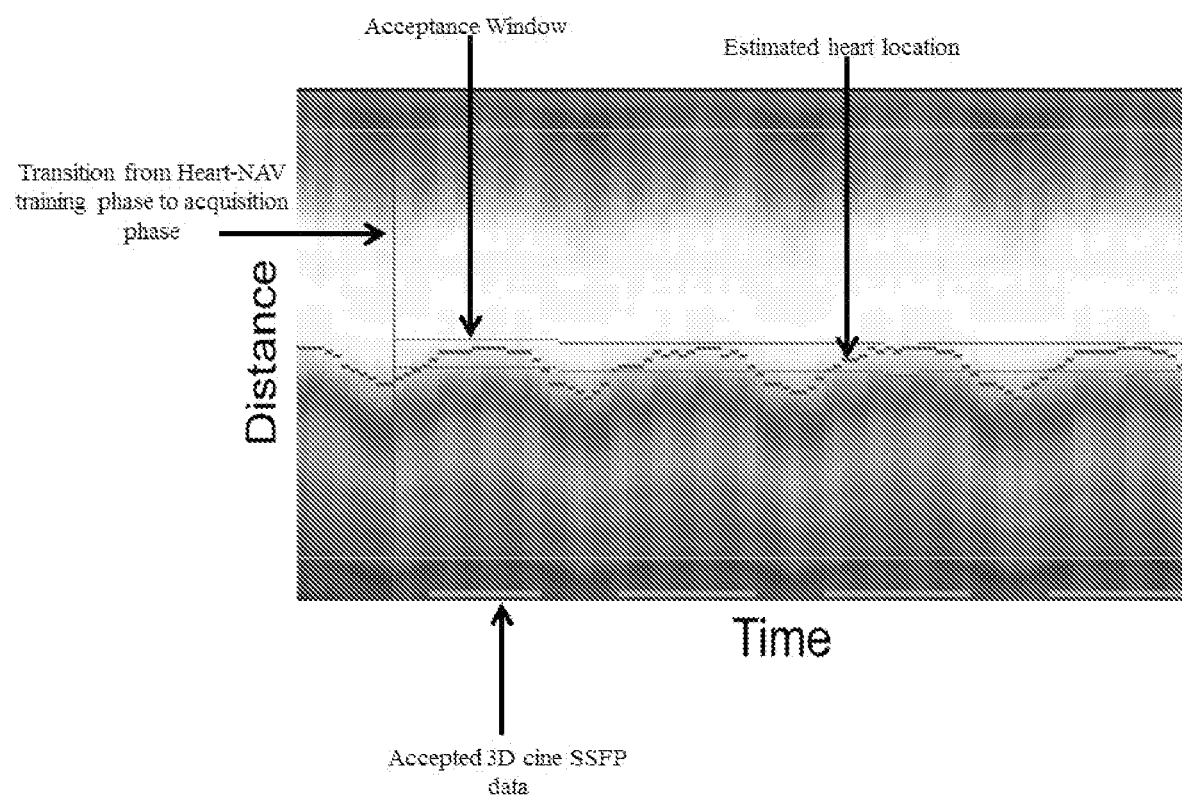
FIG. 2 shows an image of a trace of respiratory induced-heart motion measured by Heart-NAV during a 3D cine SSFP acquisition. Solid lines in the middle of the image: acceptance window (7 mm). Solid vertical line: transition from Heart-NAV training phase to acquisition phase. Horizontal dashed lines: estimated heart location. Lower solid lines: accepted 3D cine SSFP data.
Figure 4:
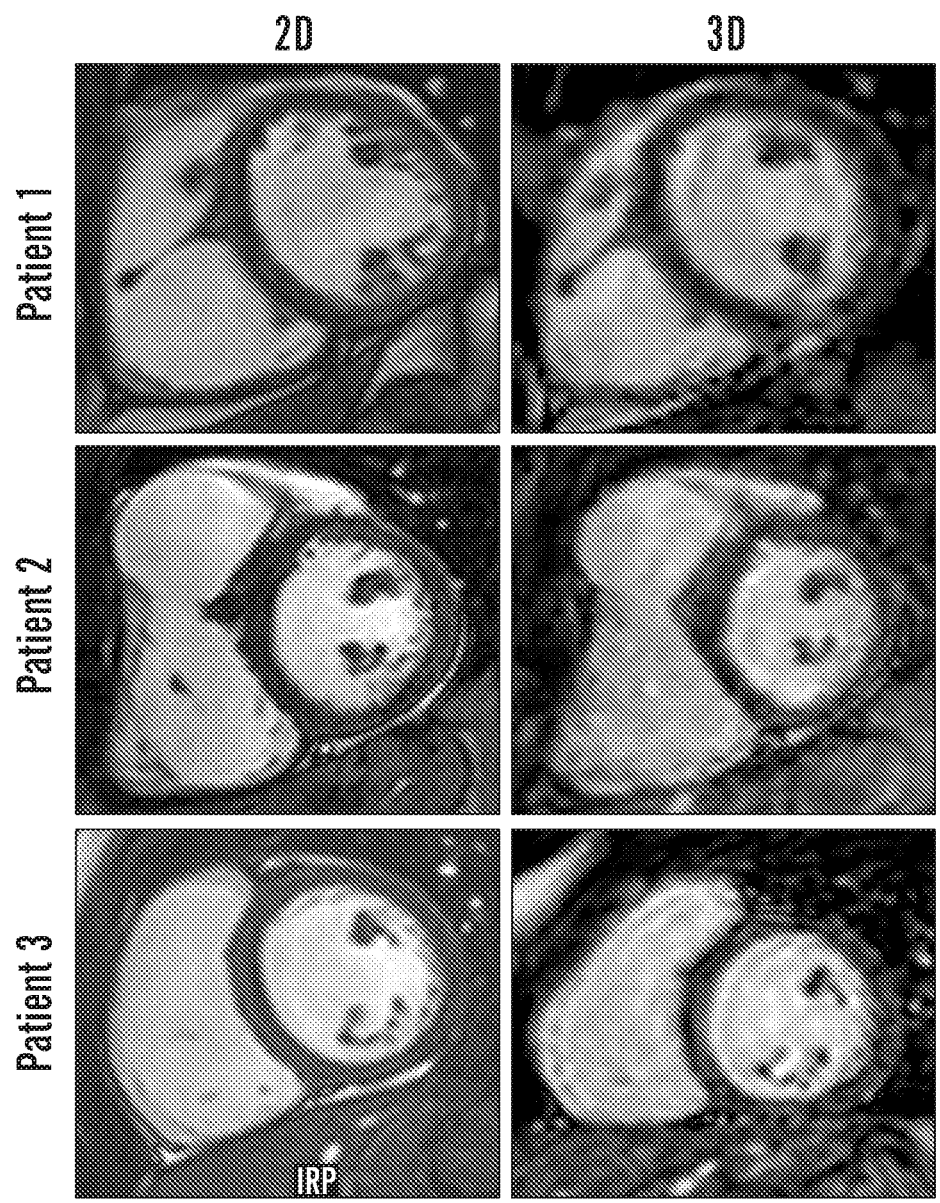
FIG. 4 shows mid-ventricular short-axis images in diastole acquired with breath-hold 2D cine SSFP and a free-breathing 3D cine SSFP with Heart-NAV from 3 patients.

A diagram of the whole-heart 3D cine SSFP sequence is shown in FIG. 1. A 3D cine SSFP sequence was prescribed in a sagittal orientation to encompass ventricles with frequency encoding in the superior-inferior direction. Standard retrospective cardiac gating was employed using a vectorcardiogram (VCG) signal. The prospective respiratory motion compensation technique is termed Heart-NAV At the beginning of every $5^{th}$ phase (i.e., segment) of the cardiac cycle, 1 radiofrequency pulse (Heart-NAV) was modified so that the phase-encoding gradient was turned off and the center line of k-space along the superior-inferior direction was read. The data from that echo was collected and transformed from the Fourier domain to the image domain, and represented the one-dimensional projection line of the 3D SSFP imaging volume in the superior-inferior orientation. The Heart-NAV image data was processed and displayed using the scanner's diaphragm navigator analysis pathway. This included a cross-correlation analysis with the preceding Heart-NAV line to measure displacement in the superior-inferior direction, and thereby prospectively gated to the respiratory cycle and adjusted (i.e., tracked) the position of the imaging volume (FIG. 2). An acceptance window at end-expiration was set during the first few seconds of the scan and the window width was pre-specified by the user. Subsequently, during the imaging phase, because all 4 Heart-NAV locations in a cardiac cycle were within the acceptance window, the acquired 3D cine data for that cardiac cycle was accepted for reconstruction; otherwise, it would have been re-acquired in the next cardiac cycle (FIG. 2, FIG. 4).

Also, it is important to note that because the Heart-NAV radiofrequency pulse excited the same volume as the pulses used for cine SSFP data, the equilibrium state of the net magnetization vector was preserved and flash artifact was avoided. Moreover, for a 3D cine SSFP sequence with 20 acquired heart phases per cardiac cycle, there will be 4 Heart-NAVs per cycle. With each Heart-NAV lasting 1 repetition time or about 3 milliseconds (ms), this leads to a total of 12 ms per cardiac cycle (spread out over the cardiac cycle) devoted to respiratory motion compensation. At a heart rate of 80 bpm or a cardiac cycle duration of 750 ms, this amounts to 1.6% of the cardiac cycle for respiratory motion compensation.

Example 2: Subjects, Image Quality and Scan Time

Seventeen patients (9 male) were enrolled in the study and all completed the protocol. The median age was 26 years (range 9-70 years), the median weight was 69 kg (range 20-107 kgs), and the mean heart rate during the MRI scan was of 76±12 bpm. Their principal diagnoses were as follows: aortic valve stenosis and/or regurgitation (n=4), repaired tetralogy of Fallot (n=4), atrial septal defect (n=2), cardiomyopathy (n=2), repaired transposition of the great arteries (n=2), connective tissue disorder (n=1), repaired double-outlet right ventricle (n=1), and Ebstein anomaly of the tricuspid valve (n=1).

Figure 3:
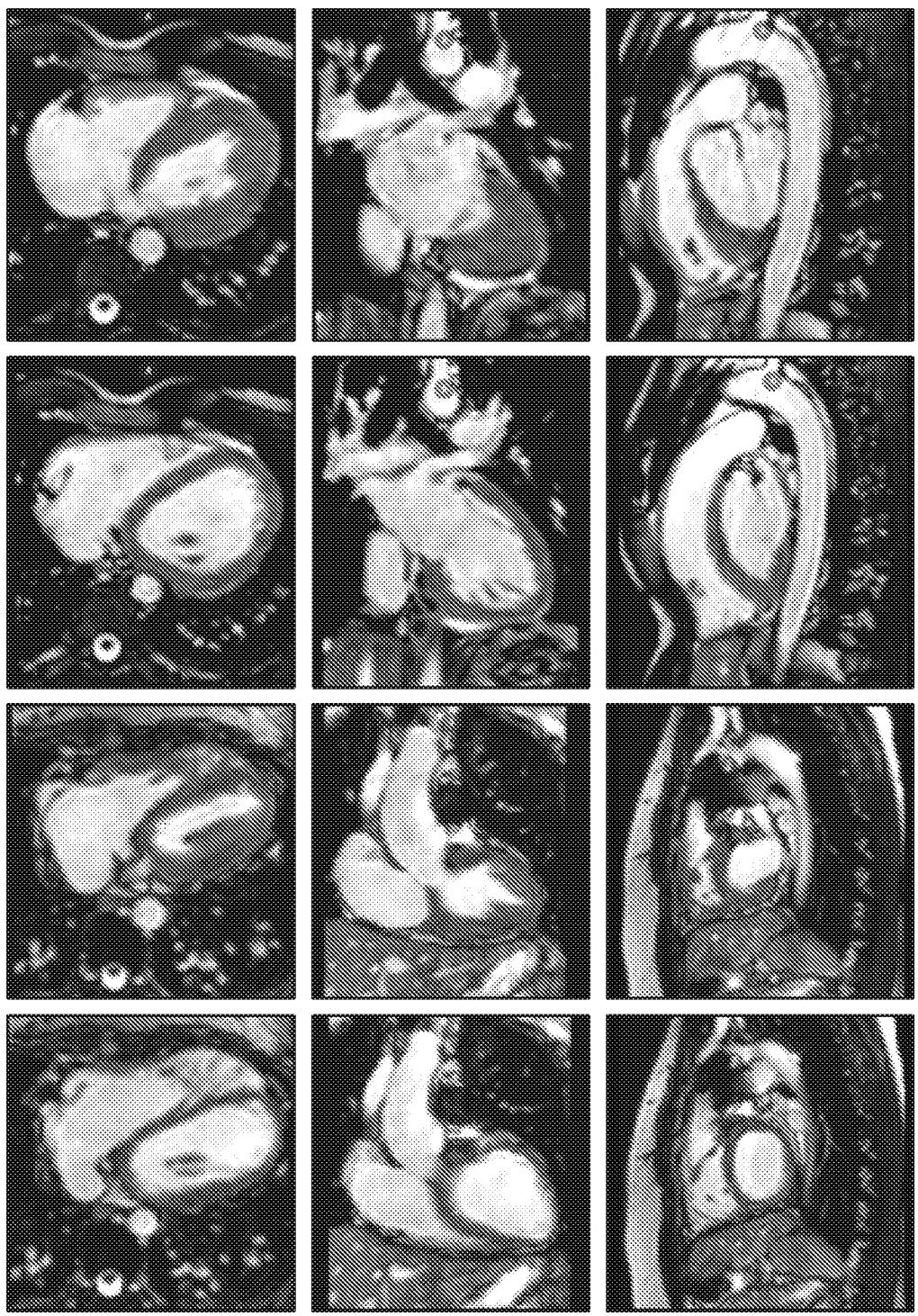
FIG. 3 shows whole-heart 3D cine SSFP images at end-diastole and end-systole in 2 patients.

Representative free-breathing 3D cine SSFP images are shown in FIG. 3. Mid-ventricular short-axis slices in diastole using breath-hold 2D cine SSFP and free-breathing 3D cine SSFP in 3 patients are compared in FIG. 4. Minimal ghosting artifact and no flashing artifact was observed. The blood and myocardium signal intensities, contrast ratio, and contrast-to-noise ratio for 2D and 3D cine SSFP are compared in Table 1, below. The myocardium signal intensity for the 2D acquisition was lower leading to a significantly better ventricular blood-to-myocardium contrast ratio and contrast-to-noise ratio. Scan time of free-breathing 3D cine sequence was 5.9±2.7 minutes.

TABLE 1

Mean blood and myocardium signal intensities, blood-to-myocardium contrast ratio (CR, and blood-to-myocardium contrast-to-noise ratio (CNR) for breath-hold 2D cine SSFP and free-breathing 3D cine SSFP acquisitions (n = 17).

|  | Blood | Myocardium | CR | CNR |
| --- | --- | --- | --- | --- |
| 2D cine SSFP | 1405 ± 262 | 273 ± 65 | 5.3 ± 1.3 | 29.1 ± 7.8 |
| 3D cine SSFP | 1324 ± 196 | 449 ± 106 | 3.1 ± 0.7 | 19.9 ± 8.4 |
| P-value | 0.223 | <0.001 | <0.001 | 0.010 |

Values are mean ± standard deviation.

Example 3: Ventricular Measurements

Figure 5:
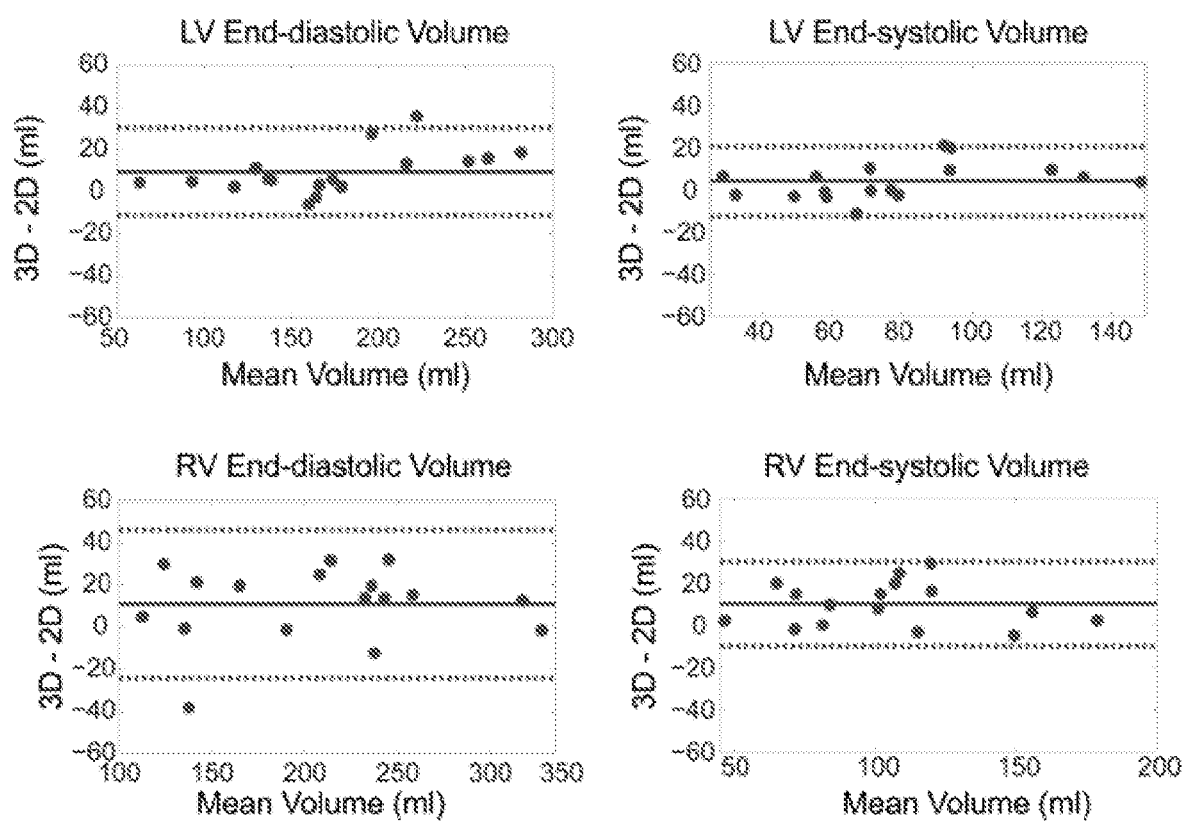
FIG. 5 depicts Bland-Altman plots of agreement comparing left and right ventricular (LV, RV) measurements for free-breathing 3D cine SSFP and conventional 2D cine SSFP. The solid line indicates the mean difference (bias) and the dashed lines show ±1.96 standard deviations of difference.

Left and right ventricular measurements for breath-hold 2D cine and free-breathing 3D cine acquisitions are compared in Table 2 and FIG. 5. Of note, 3D cine measurements of end-diastolic volume (EDV), end-systolic volume (ESV), and stroke volume (SV) for both ventricles were all larger (systematic bias); however, the differences were less than 6% except for the right ventricular ESV.

TABLE 2

Ventricular measurements for breath-hold 2D cine SSFP and free-breathing 3D cine SSFP sequences (n = 17).

|  | Left ventricle | | | | Right ventricle | | | |
| --- | --- | --- | --- | --- | --- | --- | --- | --- |
|  | EDV (ml) | ESV (ml) | SV (ml) | EF (%) | EDV (ml) | ESV (ml) | SV (ml) | EF (%) |
| 2D cine SSFP | 168.6 ± 56.9 | 76.2 ± 31.7 | 92.3 ± 28.8 | 55.4 ± 6.6 | 202.0 ± 64.2 | 96.1 ± 38.5 | 105.9 ± 32.1 | 53.2 ± 8.2 |
| 3D cine SSFP | 178.1 ± 62.8 | 80.2 ± 34.8 | 97.9 ± 31.1 | 55.8 ± 5.8 | 212.9 ± 66.1 | 106.2 ± 37.1 | 109.7 ± 32.0 | 51.1 ± 7.9 |
| Mean difference (3D − 2D) | 9.5 ± 10.6 | 4.0 ± 8.5 | 5.5 ± 9.2 | 0.5 ± 4.4 | 10.9 ± 17.9 | 10.1 ± 10.2 | 3.8 ± 9.8 | −2.1 ± 3.3 |
| Mean % difference (3D − 2D) | 5.1 ± 4.9% | 4.3 ± 7.4% | 6.0 ± 9.4% | 1.0 ± 7.8% | 5.3 ± 11.2% | 11.7 ± 11.9% | 3.9 ± 9.9% | −2.0 ± 3.0% |

Values are mean ± standard deviation.
EDV, end-diastolic volume;
EF, ejection fraction;
ESV, end-systolic volume; and
SV, stroke volume.

Disclosed herein is a new prospective respiratory motion compensation method (Heart-NAV) for cardiovascular magnetic resonance imaging of a subject in a free-breathing whole-heart 3D cine SSFP sequence. This method was developed and evaluated in patients. Heart-NAV leverages the scanner's existing diaphragmatic navigator technology, preserves the equilibrium state of the net magnetization vector preventing flash artifact, is compatible with retrospective cardiac gating, and occupies only 1.6% of cardiac cycle. In a prospective evaluation in patients, all 3D cine SSFP acquisitions were successful and the mean scan time was 5.9 minutes. Ventricular volumes from 3D cine SSFP were slightly larger than those from a conventional breath-hold 2D cine acquisition. The myocardial signal was relatively brighter in the 3D cine SSFP images, leading to lower blood-to-myocardium contrast ratio and contrast noise ratio compared to 2D cine images.

Left and right ventricular volumes by 3D cine SSFP were all larger than those from 2D cine SSFP. This bias was <6% except for right ventricular ESV which was 12%, and all biases were in the range observed for inter-scan variability in patients with congenital heart disease (Blalock S. E. et al., J Magn Reson Imaging 2013; 38(4):829-835). The temporal resolution of the 3D and 2D cine data was the same, and reformatting of the 3D data was done to match the orientation and slice number of the 2D data. However, the 3D data had a lower in-plane spatial resolution and was acquired after gadobutral, a contrast agent, was administered. Both of these differences have been associated with higher ventricular volume measurements (Miller S. et al., Radiology 2002; 223(1):263-269; Matthew S. et al., Br J Radiol. 2012; 85(1015):e343-347). In addition, although both image datasets were acquired at end-expiration, it is possible that the different breathing patterns (breath-holding versus free-breathing) contributed to the bias in volume calculation.

Several factors influenced the signal intensity of blood and myocardium in this study. In the 2D cine acquisition, blood flow through the imaging plane contributed to the bright signal of the ventricular blood pool (Nezafat R. et al., J Magn Reson Imaging 2008; 28(5):1273-1279). In the 3D cine acquisition, the larger volume of excitation led to a saturation of inflowing blood, a darker blood pool, and inferior image quality (Nezafat R. et al., J Magn Reson Imaging 2008; 28(5):1273-1279). Thus, it was chosen to mitigate the saturation effect by performing 3D cine SSFP imaging after administering a T1-shortening intravenous contrast agent. Although this increases the blood pool signal and the quality of 3D cine SSFP imaging, the contrast agent also perfuses into the myocardium and increases its signal as well. This caused a lower blood-to-myocardium contrast ratio and contrast noise ratio for the 3D cine images compared to the 2D cine images, which were performed before the contrast agent was administered.

The Heart-NAV approach for free-breathing 3D cine SSFP acquisition as disclosed herein has many advantages relative to other methods of cardiac imaging. Although it is compatible with non-linear k-space profile orderings, the current version uses a conventional Cartesian k-space trajectory that makes fast in-line image reconstruction on the scanner possible and allows for the application of existing parallel imaging techniques. These features are important because they facilitate implementation in the clinical environment and dissemination to other sites to explore the utility and robustness of 3D cine imaging. In contrast to the external respiratory bellows belt approach, Heart-NAV tracks the heart position and prospectively adjusts the imaging plane according to position within the acceptance window. Lastly, by using only 12 ms per heartbeat for respiratory motion compensation, the Heart-NAV approach temporally samples nearly the full cardiac cycle.

Based on this experience, the image quality was encouraging for clinical application, robustness, and clinical practicality of free-breathing whole-heart 3D cine acquisitions using Heart-NAV. It is easy to plan, has an acceptable scan time, eliminates the drawbacks of breath-holding, and provides the reformatting advantages of a volume dataset. Looking forward, the Heart-NAV technique is amenable to further refinements. In the current implementation, the Heart-NAV signal is received by the body coil and includes static signal from the chest and spine adjacent to the heart. The fidelity of the Heart-NAV signal could be improved by using an anterior phased array coil element which is closer to the heart to receive the signal and thereby suppress the surrounding static signal (Piccini D. et al., Magn Reson Med 2012; 68(2):571-579). Furthermore, the scan time of 3D cine acquisition can be shortened by using compressed sensing image reconstruction (Uecker M. et al., Magn Reson Med 2014; 71(3):990-1001) and respiratory biofeedback (Hamlet S. M. et al., J Cardiovasc Magn Reson 2016; 18(1):54). This increased efficiency could be traded for further improvements in spatial or temporal resolution.

In closing, disclosed herein is a new prospective respiratory motion compensation algorithm, Heart-NAV, for free-breathing whole-heart 3D cine SSFP imaging. Ventricular volume measurements using this technique were slightly larger than those obtained with a conventional breath-hold 2D cine SSFP acquisition, and scan time was within a clinically acceptable range. Such 3D cine acquisitions eliminate the need for breath-holding, simplify scanning, and enable volume-based reformatting and analysis.

Example 4: Fusing 3D Cine SSFP with 3D Cine Phase Contrast

The typical cardiac magnetic resonance imaging examination uses multiple 2D steady-state free precession (SSFP) and phase contrast (PC) sequences with repeated breath-holds. It requires careful planning of multiple imaging planes by a knowledgeable operator and yields blurred images in patients who are too young or ill to hold their breath. To address these deficiencies, a simply-planned, comprehensive, free-breathing 3D cine SSFP and 3D cine phase contrast cardiac magnetic resonance examination was developed and tested.

The 3D cine SSFP and 3D cine phase contrast sequences both can utilize the disclosed "Heart-NAV" technique for prospective respiratory motion compensation. Specifically, four excitations per cardiac cycle are re-purposed to generate a one-dimensional signal that is routed into the scanner's standard navigator processing system to track heart position. If all four signals are in end-expiration, cine data from the entire cardiac cycle is accepted.

In the proposed approach, both 3D cine sequences would be acquired in the sagittal plane with an isotropic resolution of 2.0 mm$^3$ and 30 phases per cardiac cycle. This would facilitate off-line superposition of the phase contrast images over the SSFP images using a rigid-body registration algorithm. The result would result in a fused 3D cine dataset with the superior contrast-to-noise ratio of SSFP imaging and co-registered, superimposable flow data.

To assess this approach, 15 patients (8 males, median age 18 years (range 11-58)) with informed consent underwent both a clinical 2D cardiac magnetic resonance study plus the two proposed 3D cine sequences on a 1.5T Philips Achieva scanner. First, the breath-hold 2D cine SSFP and free-breathing 2D cine phase contrast sequences were acquired. Then, after receiving 0.15 mmol/kg gadobutrol contrast, the novel 3D cine SSFP (flip angle 60°, TE/TR 1.5/3.0 ms, SENSE×3), and 3D cine phase contrast (flip angle 8°, TE/TR 2.1/3.8 ms, SENSE×4) sequences were performed. For comparison of ventricular parameters, the 3D cine SSFP data was reformatted into a short-axis plane.

Figure 7:
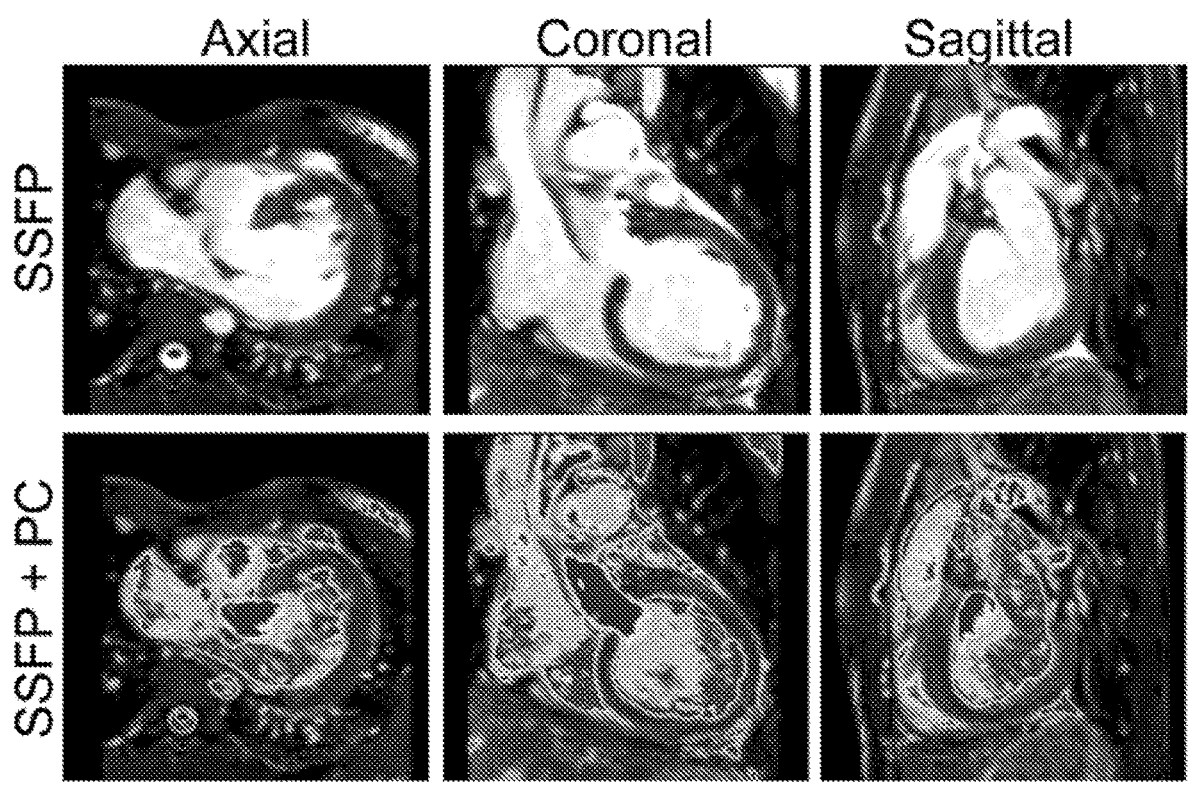
FIG. 7 provides 3D cine steady-state free precession (SSFP) image acquisitions (top row) and its fusion with a 3D cine phase contrast (PC) acquisition (i.e., velocity data) in axial, coronal, and sagittal orientations. The shading represents the magnitude of the velocity vector.

All 3D acquisitions were successfully completed. A 3D cine SSFP acquisition and its fusion with 3D cine flow data are shown in FIG. 7. The scan time was 6.3±1.8 min for 3D cine SSFP and 12.8±4.8 min for 3D cine phase contrast. The mean 3D cine SSFP to 3D cine PC registration offset was 1.5±0.98 mm and 0.01±0.03°. The differences between 2D and 3D measurements of left ventricular parameters, ascending aorta and main pulmonary artery net blood flow, and Qp/Qs were all ≤9% (Table 3).

acquisition parameters were as follows: field-of-view 260× 260 mm, in-plane resolution 1.8×1.8 mm reconstructed to 1.25×1.25 mm, slice thickness 8 mm, slice gap 0-2 mm, flip angle 60°, echo time 1.4 ms, repetition time 2.8 ms, bandwidth 1.1 kHz, heart phases 20 interpolated to 30, and SENSE factor 2. Three to 10 minutes after the administration of 0.15 mmol/kg gadobutral contrast, a free-breathing 3D cine SSFP sequence with Heart-NAV for respiratory motion compensation was acquired in a sagittal plane with the following parameters: field-of-view 512×250×180 mm, isotropic resolution 2.0 mm$^3$, flip angle 60°, echo time 1.5 ms, repetition time 3.0 ms, bandwidth 1.7 kHz, heart phases 20 interpolated to 30, respiratory acceptance window 7 mm, tracking factor 1, and SENSE factor 3 (2 anterior-posterior direction, 1.5 right-to-left direction). The scan time of the 3D cine SSFP sequence was measured prospectively with a stopwatch.

TABLE 3

Comparison of 2D and 3D cine sequences for left ventricular and blood flow measurements (n = 15).

|  | EDV (ml) | ESV (ml) | SV (ml) | EF (%) | Mass (g) | AAo Net flow (ml) | MPA Net flow (ml) | $Q_p/Q_s$ |
| --- | --- | --- | --- | --- | --- | --- | --- | --- |
| 2D | 169.9 ± 59.3 | 71.1 ± 28.3 | 98.7 ± 34.9 | 58.6 ± 7.4 | 97.0 ± 32.9 | 82.7 ± 33.6 | 84.6 ± 31.8 | 1.0 ± 0.1 |
| 3D | 175.7 ± 61.8 | 78.2 ± 31.8 | 97.6 ± 32.2 | 56.3 ± 6.1 | 102.2 ± 35.3 | 83.6 ± 38.3 | 77.2 ± 31.8 | 1.0 ± 0.2 |
| Mean difference (3D − 2D) | 5.9 ± 8.6 | 7.0 ± 7.3 | −1.2 ± 7.9 | −2.3 ± 3.3 | 5.3 ± 9.9 | 0.9 ± 16.1 | −7.4 ± 15.3 | −0.1 ± 0.2 |
| Mean % difference (3D − 2D) | 3.4 ± 5.5 | 9.3 ± 9.5 | −0.3 ± 8.1 | −3.7 ± 5.6 | 5.8 ± 11.8 | −0.1 ± 18.8 | −8.9 ± 21.4 | −8.8 ± 22.9 |
| Correlation (3D vs. 2D) | 0.99 | 0.98 | 0.98 | 0.90 | 0.96 | 0.91 | 0.88 | −0.03 |
| P-value (3D vs. 2D) | 0.009 | 0.001 | 0.291 | 0.009 | 0.029 | 0.414 | 0.042 | 0.125 |

Values are mean ± standard deviation.
AAo, ascending aorta;
EDV, end-dsastolic volume;
EF, ejection fraction;
ESV, end-systolic volume;
MPA, main pulmonary artery, and
SV, stroke volume.

A free-breathing 3D cine SSFP and 3D cine phase contrast cardiac magnetic resonance examination with a scan time of about 20 minutes was developed and tested in patients, and good agreement was found with 2D left ventricular and blood flow measurements. The single fused isotropic 3D cine dataset is well-suited for multiplanar reformatting, and provides a comprehensive anatomic and functional assessment. This strategy simplifies exam planning and eliminate breath-holding.

The results described herein were obtained using the following materials and methods.

Subjects

To evaluate the whole-heart 3D cine SSFP sequence with Heart-NAV respiratory motion compensation in clinical practice and compare it to the conventional 2D cine SSFP acquisition, a prospective study was performed. Subjects were eligible if they were referred for a cardiovascular MRI examination with administration of a contrast agent and did not require sedation. The Boston Children's Hospital Committee on Clinical Investigation approved this study, and written informed consent was obtained from all subjects.

Cardiovascular MRI Protocol

MRI examinations were performed with a 1.5T Achieva dStream scanner (Philips Healthcare, Best, the Netherlands) and vectorcardiogram gating. In each subject, a conventional breath-hold 2D cine SSFP sequence was used to acquire a stack of 12 slices prescribed in a ventricular short-axis plane to completely encompass the left and right ventricles. The Image Analysis The 2D and 3D cine images were reconstructed in-line on the scanner and then transferred to a workstation where they were analyzed using commercially available software (CVI$^{42}$, Circle Cardiovascular Imaging, Calgary, Canada). The 3D cine images were reformatted into a short-axis, 2-chamber, 3-chamber and 4-chamber views. The orientation, number, thickness, and interslice gap of reformatted short-axis slices were matched to the 2D cine short-axis parameters for each subject. A single observer delineated the right and left ventricular myocardial boundaries on the short-axis 2D cine and reformatted 3D cine images, and was blinded to the numeric results. Left and right ventricular end-diastolic volume (EDV), end-systolic volume (ESV), stroke volume (SV), and ejection fraction (EF) were calculated using a standard summation of disks approach.

The ventricular blood-to-myocardium contrast ratio (CR) (Hamdan A. et al., J Magn Reson Imaging 2008; 27(5): 1028-1036) and contrast-to-noise ratio (CNR) (Arai A. E. et al., J Magn Reson Imaging 1999; 10(5):771-777) were calculated as follows:

$$CR = \frac{\overline{S}_{blood}}{\overline{S}_{myocardium}},$$

$$CNR = \frac{2 \times (\overline{S}_{blood} - \overline{S}_{myocardium})}{(SD_{blood} + SD_{myocardium})},$$

where S is the signal intensity and SD is the standard deviation of the signal within the specified region of interest (ROI). The ROI for blood was positioned in the center of the left ventricular cavity at end-diastole, and the ROI for myocardium was positioned in the ventricular septum at the mid-ventricular level at end-diastole. Because SENSE was used for image reconstruction, the noise was calculated as the standard deviation of the signal intensity in the respective ROIs, and the signal-to-noise ratio could not be assessed (Makowski M. R. et al., J Cardiovasc Magn Reson 2012; 14(1):53).

Statistical Analysis

Descriptive statistics are reported as median and range, or mean±standard deviation, as appropriate. A paired two-tailed Student's t-test was used to compare the tissue signal intensities, CR, and CNR; a p-value ≤0.05 was considered statistically significant. Bland-Altman analysis was used to assess agreement (Bland J. M. et al., Lancet 1986; 1(8476): 307-310). The mean of the differences (3D-2D) and mean of the differences expressed as a percentage $$\left(\frac{3D-2D}{0.5 \times (3D+2D)} \times 100\right)$$

were calculated.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for obtaining a three-dimensional reconstruction of a heart in a freely respiring subject, the method comprising
controlling a medical imaging device to utilize a first sequence of a first plurality of scanning signals to acquire three-dimensional images of the heart in a cardiac cycle during respiration of a subject, wherein each scanning signal in the first sequence of the first plurality of scanning signals comprises a phase-encoding gradient to capture ventricles in an imaging volume along a superior-inferior direction;
controlling the medical imaging device to utilize a second sequence of a second plurality of scanning signals to acquire three-dimensional images of blood flow data in a cardiac cycle during respiration of the subject, wherein each scanning signal in the second sequence of the second plurality of scanning signals comprises a phase contrast to capture blood flow in the ventricles in the imaging volume along the superior-inferior direction;
controlling, upon completion of the sequence, the medical imaging device to turn off the phase-encoding gradient to produce a center line scanning signal to acquire, during the cardiac cycle, a one-dimensional projection line on the imaging volume;
identifying the one-dimensional projection line as a center line in k-space during the cardiac cycle in the superior-inferior direction during respiration;
determining a maximal superior displacement of the heart that defines a respiratory acceptance window having a specified width;
selecting a series of the three-dimensional images of the heart and a series of the three-dimensional images of the blood flow data that fall within the acceptance window for use in reconstruction; and
fusing the series of the three-dimensional images of the heart and the series of the three-dimensional images of the blood flow data based on alignment according to the maximal superior displacement of the heart, thereby compensating for respiratory-induced motion to obtain a three-dimensional reconstruction of the heart.

2. A method for obtaining a three-dimensional reconstruction of a heart in a freely respiring subject, the method comprising:
tracking the respiratory-induced motion of the heart in the superior-inferior direction during the course of respiration of the subject using 3D cine steady-state free precession (SSFP) imaging, wherein the respiratory-induced motion is acquired during a four radio-frequency image excitation; and
fusing blood flow data with the 3D cine SSFP imaging, the blood flow data being indicative of blood flow through the heart during the course of respiration of the subject, wherein the blood flow data is acquired by controlling a medical imaging device to utilize a second sequence of a second plurality of scanning signals to acquire three-dimensional images of the blood flow data in a cardiac cycle during respiration of the subject, wherein each scanning signal in the second sequence of the second plurality of scanning signals comprises a phase contrast to capture blood flow in the ventricles in the imaging volume along the superior-inferior direction.

3. The method of claim 1, wherein the images are acquired using cardiovascular magnetic resonance imaging, ultrasound, or computerized tomography (CT) scan.

4. The method of claim 3, wherein image acquisition is carried out using three-dimensional (3D) cine SSFP sequence imaging to produce the imaging volume as a 3D cine SSFP imaging volume.

5. The method of claim 4, wherein a radiofrequency pulse is modified so that the phase-encoding gradient is turned off and the center line of k-space along the superior-inferior direction is read.

6. The method of claim 5, wherein the method is carried out at a beginning of every $5^{th}$ phase segment of the cardiac cycle.

7. The method of claim 4, wherein a plot comprises a one-dimensional projection line of the 3D cine SSFP imaging volume in the superior-inferior direction.

8. The method of claim 1, wherein the width of the respiratory acceptance window is between about 3 and about 20 mm.

9. The method of claim 4, wherein a scan time of 3D cine acquisition is shortened by parallel imaging with sensitivity encoding (SENSE).

10. The method of claim 4, wherein the 3D cine SSFP is acquired in a sagittal orientation.

11. The method of claim 1, wherein the images have a lower ventricular blood-to-myocardium contrast ratio and contrast-to-noise ratio than images acquired via short-axis 2D cine.

12. The method of claim 1, wherein the method is compatible with retrospective cardiac gating.

13. The method of claim 1, wherein the method is carried out after administration of a contrast agent to the subject.

14. The method of claim 13, wherein the contrast agent is extracellular or intravascular.

15. The method of claim 14, wherein the contrast agent is gadolinium-based.

16. The method of claim 15, wherein the gadolinium-based contrast agent is selected from the group consisting of gadoterate, gadodiamide, gadobenate, gadopentetate, gadoteridol, gadoversetamide, gadoxetate, gadobutrol, and gadofosveset.

17. The method of claim 1, wherein the subject is a child, is anesthetized, or is otherwise incapable of holding their breath.

18. The method of claim 1, wherein the method characterizes a cardiovascular disorder selected from the group consisting of tissue damage associated with a heart attack, reduced blood flow in heart muscle, cardiac function and ejection fraction, aortic tears, aneurysms, narrowing, cardiomyopathy, diseases of a pericardium, heart disease, heart valve disorders, congenital heart problems, connective tissue disorders.

19. The method of claim 1, wherein the method characterizes a surgical repair of the heart.

20. A method for obtaining a three-dimensional reconstruction of a heart in a freely respiring subject, the method comprising controlling a medical imaging device to utilize a sequence of a plurality of scanning signals to acquire three-dimensional images of the heart in a cardiac cycle during respiration of a subject, wherein each scanning signal in the sequence of the plurality of scanning signals comprises a phase-encoding gradient to capture ventricles in an imaging volume along a superior-inferior direction;

controlling the medical imaging device to utilize a second sequence of a second plurality of scanning signals to acquire three-dimensional images of blood flow data in a cardiac cycle during respiration of the subject, wherein each scanning signal in the second sequence of the second plurality of scanning signals comprises a phase contrast to capture blood flow in the ventricles in the imaging volume along the superior-inferior direction;

controlling, upon completion of the sequence, the medical imaging device to turn off the phase-encoding gradient to produce a center line scanning signal to acquire, during the cardiac cycle, a one-dimensional projection line on the imaging volume;

identifying the one-dimensional projection line as a center line in k-space during the cardiac cycle in the superior-inferior direction during respiration;

determining a maximal superior displacement of the heart that defines a respiratory acceptance window having a specified width;

selecting a series of the three-dimensional images of the heart that fall and a series of the three-dimensional images of the blood flow data within the acceptance window for use in reconstruction;

fusing the series of the three-dimensional images of the heart; and fusing the series of the three-dimensional images of the heart and the series of the three-dimensional images of the blood flow data based on alignment according to the maximal superior displacement of the heart, thereby obtaining a three-dimensional reconstruction of the heart.

\* \* \* \* \*